(12) United States Patent
Jessop

(10) Patent No.: US 9,955,684 B2
(45) Date of Patent: *May 1, 2018

(54) COATING COMPOSITION FOR PATHOGEN CONTROL IN VEGETABLES

(75) Inventor: Nicholas Hugh Hylton Jessop, Winchester (GB)

(73) Assignee: Exosect Limited, Winchester, Hants (GB)

( * ) Notice: Subject to any disclaimer, the term of this patent is extended or adjusted under 35 U.S.C. 154(b) by 146 days.

This patent is subject to a terminal disclaimer.

(21) Appl. No.: 14/112,579

(22) PCT Filed: Apr. 19, 2012

(86) PCT No.: PCT/GB2012/000360
§ 371 (c)(1),
(2), (4) Date: Nov. 1, 2013

(87) PCT Pub. No.: WO2012/143678
PCT Pub. Date: Oct. 26, 2012

(65) Prior Publication Data
US 2014/0045688 A1   Feb. 13, 2014

(30) Foreign Application Priority Data
Apr. 20, 2011 (GB) .................................. 1106747.7

(51) Int. Cl.
| | | |
|---|---|---|
| A01N 25/08 | (2006.01) |
| A01N 63/04 | (2006.01) |
| A01N 25/12 | (2006.01) |
| A01N 25/00 | (2006.01) |
| C09D 191/06 | (2006.01) |
| A01N 25/24 | (2006.01) |
| C09D 5/14 | (2006.01) |

(52) U.S. Cl.
CPC ............. *A01N 25/12* (2013.01); *A01N 25/00* (2013.01); *A01N 25/08* (2013.01); *A01N 25/24* (2013.01); *C09D 5/14* (2013.01); *C09D 191/06* (2013.01); *C08L 2205/18* (2013.01)

(58) Field of Classification Search
None
See application file for complete search history.

(56) References Cited

U.S. PATENT DOCUMENTS

| | | | | |
|---|---|---|---|---|
| 3,151,969 A * | 10/1964 | Stevens | .................. | A01N 25/26 504/189 |
| 3,905,152 A * | 9/1975 | Loperfido | ................ | A01C 1/06 47/57.6 |
| 4,251,952 A * | 2/1981 | Porter | ....................... | A01C 1/06 47/57.6 |
| 4,297,339 A | 10/1981 | Craven | | |
| 4,879,839 A * | 11/1989 | Gago | ....................... | A01C 1/06 427/4 |
| 5,283,060 A | 2/1994 | Shieh | | |
| 6,221,375 B1 * | 4/2001 | Howse | .......................... | 424/417 |
| 2003/0108584 A1 | 6/2003 | Priesnitz et al. | | |
| 2007/0072775 A1 | 3/2007 | van Boxtel-Verhoeven et al. | | |
| 2007/0207927 A1 | 9/2007 | Rosa et al. | | |
| 2008/0207448 A1 * | 8/2008 | Marx | ....................... | A01C 1/06 504/100 |
| 2009/0143447 A1 | 6/2009 | Arthur et al. | | |
| 2010/0112060 A1 * | 5/2010 | Maor et al. | ................... | 424/484 |
| 2010/0291231 A1 | 11/2010 | Stadler et al. | | |
| 2013/0101655 A1 * | 4/2013 | Storm et al. | .................. | 424/409 |

FOREIGN PATENT DOCUMENTS

| | | |
|---|---|---|
| CN | 1288661 A | 3/2001 |
| DE | 199 06 491 A1 | 8/2000 |
| GB | 2268676 A | 1/1994 |
| GB | 2425954 A | 11/2006 |
| GB | 2481881 A | 1/2012 |
| WO | 97/33472 A1 | 9/1997 |
| WO | 01/78509 A2 | 10/2001 |
| WO | 03051112 A1 | 6/2003 |
| WO | 2005/077169 A1 | 8/2005 |
| WO | 2007/005470 A2 | 1/2007 |
| WO | 2007/072046 A2 | 6/2007 |
| WO | WO-2009124707 A2 * | 10/2009 ............. A01N 63/00 |
| WO | WO 2010106314 A2 * | 9/2010 ............. A01N 25/22 |
| WO | WO-2010107312 A1 * | 9/2010 ............. A01C 1/06 |
| WO | 2011/128639 A2 | 10/2011 |
| WO | 2011/148144 A1 | 12/2011 |

OTHER PUBLICATIONS

J.E. Eger, Jr., "Utility of Spinosad for Insect Control in Florida Vegetables," Proc. Fla. State Hort. Soc. 111:55-57. 1998.*
S.P. Wraight et al., "Comparative virulence of Beauveria bassiana isolates against lepidopteran pests of vegetable crops," Journal of Invertebrate Pathology 103 (2010) 186-199.*
"Solid," <https://www.merriam-webster.com/dictionary/solid>, © 2017 Merriam-Webster, incorporated, p. 2.*
International Search Report for PCT/GB2012/000360 dated Jan. 16, 2013.
Search Report for GB1206943.1 dated Aug. 17, 2012.
"Exosect: an innovative electrostatic technology providing environmentally friendly pest control" University of Southampton Web
(Continued)

*Primary Examiner* — Tracy Vivlemore
*Assistant Examiner* — Monica A Shin
(74) *Attorney, Agent, or Firm* — Sughrue Mion, PLLC

(57) ABSTRACT

Coating composition for applying to a vegetable plant structure such as a seed of a vegetable plant from which roots and shoots are capable of growing, wherein the said coating composition comprises an organic carrier material in particulate form and one or more biological agents that possess an activity against at least one or more pathogens of the said vegetable plant.

14 Claims, 1 Drawing Sheet

(56) References Cited

OTHER PUBLICATIONS

Archive; Centre for Biological Sciences; XP055266408; (Nov. 26, 2013) 4 pages total.

* cited by examiner

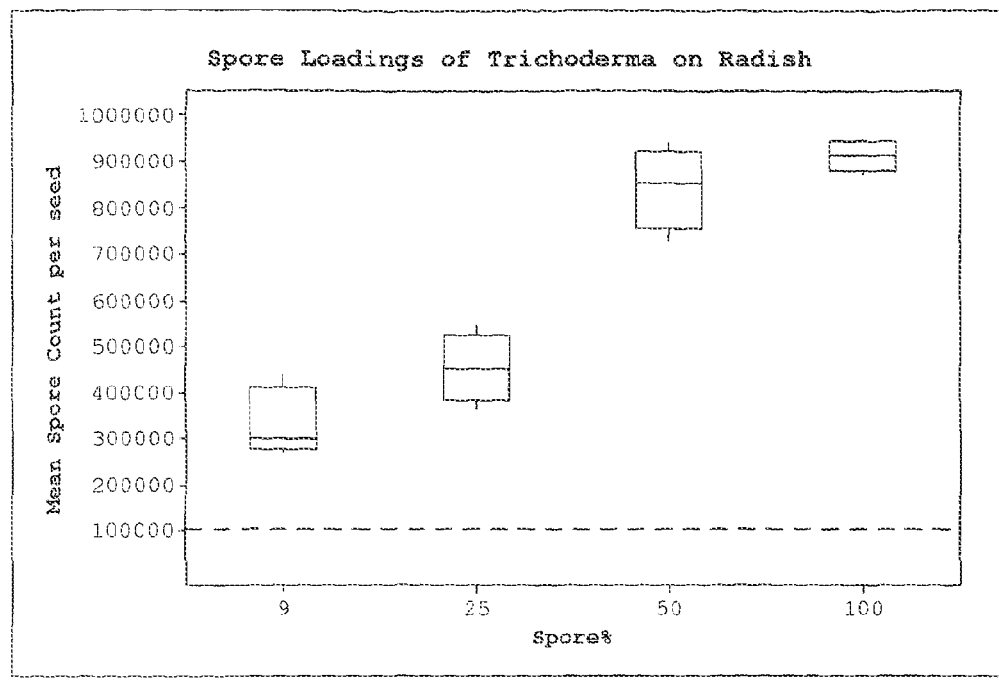

COATING COMPOSITION FOR PATHOGEN CONTROL IN VEGETABLES

CROSS REFERENCE TO RELATED APPLICATIONS

This application is a National Stage of International Application No. PCT/GB2012/000360, filed on Apr. 19, 2012, which claims priority from British Patent Application No. 1106747.7, filed on Apr. 20, 2011, the contents of all of which are incorporated herein by reference in their entirety.

The present invention relates to coating compositions including an organic component and a biological agent for applying to plant structures of vegetable plants from which roots and shoots are capable of growing, uses of coating compositions on vegetable plant structures, methods of producing such coating compositions and plant structures coated with such coating compositions. In particular, the invention relates to coating compositions that comprise an organic carrying material and biological agents selected from chemicals and biological agents active against one of more plant pathogens selected from bacterial, fungal and arthropod pathogens that infest plant structures of vegetable plants.

Losses in yield in vegetable plant crops are recorded annually and come about as a result of plant infestations due to pathogens such as bacteria, fungi and arthropods which can infest the plant at various stages of development, such as at the seed stage. Agronomic losses due to pathogen infestations remain high despite many defensive measures that have been devised by man to combat such infestations. Such defensive measures include the use of synthetic chemicals; the employment of genetic engineering of plants; and the use of live biological agents that are applied in the form of coatings, sprays and washes to vegetable plant structures such as seeds and bulbs.

Pesticides in the form of chemical agents such as fungicides, bactericides and arthropodicides, typically in the form of insecticides and/or acaricides may be applied to vegetable plant crops in the form of soil drenches, liquid seed treatments and the like. Such kinds of chemical treatments tend to be indiscriminate and may adversely affect beneficial bacteria, fungi and arthropods as well as the plant pathogens at which such treatments are targeted.

When conventional pesticides are used as seed treatments the seeds are coated with pesticide directly or the pesticide is applied to the seed in the presence of an inorganic carrier. Such seed treatments are typically applied in liquid form or as wet slurry and subsequently the seeds are dried. Such treatments are mostly aimed at providing direct protection against pathogens such as arthropods and/or seed borne microorganisms and/or soil borne microorganisms that attack the seed. The high level of chemicals that are typically used introduces a chemical load to the environment that may give rise to ecological concerns.

One problem in applying a biological agent that is a chemical agent in conventional seed coating procedures is that the chemical agent is typically applied as slurry and this may give rise to an uneven application of the coating whereby the seeds are not fully coated or a percentage of the seeds, up to 20% depending on seed type and the coating procedure employed, do not get fully coated. Furthermore, the seed coatings may not be uniform and this gives rise to physical weaknesses in the seed coat and the coating may flake off.

A further problem arises when using biological agents that are selected from beneficial live bacterial and fungal species that may be applied conventionally to plant structures such as seeds, for example as spores in conjunction with an inorganic carrier in the form of particulate compositions or in the form of liquid compositions which may then be dried back, is that the applied biological agents rapidly lose viability. Without the intention of being bound by theory it is thought that as the seeds or storage organs such as bulbs are dried off, the micro-environment alters and the viability of applied live biological agents may be seen to decrease sharply and almost as soon as the applied composition dries. The loss of viability of the biological agent is typically associated with the splitting of the fungal or bacterial spores which renders them non-viable.

It has now been found that by using an organic carrier material in conjunction with a biological agent, the viability of the biological agent is improved on vegetable plant structures such as seeds and bulbs, relative to the viability of biological agents applied to such seeds conventionally. Furthermore, the coating of the plant structure is less susceptible to flaking off.

It is an object of the present invention to supply improved coatings comprising biological agents for vegetable plant structures, such as seeds. Furthermore, it is an object of the invention to supply seed coatings that utilise fewer chemical additives and/or lesser amounts of thereof for protecting seed and/or young plantlets from pathogens than conventional seed coatings.

These and other objects of the invention will become apparent from the following description and examples.

According to the present invention there is provided a vegetable plant structure coating composition, wherein the said coating composition comprises at least one organic carrier material in the form of particles wherein the carrier material is selected from waxes having a melting point of ≥50° Centigrade and one or more biological agents that possess an activity against one or more pathogens of a vegetable plant.

Farm-produced crops are typically destined for many diverse markets such as food for human consumption and in the production of fodder for domesticated livestock, such as chickens and cattle. For the purposes of the present invention a "vegetable plant structure" is one from which roots and shoots are able to grow. Such structures are typically bulbs, roots, seeds and "seed tubers". Reference to "seed" and "seeds" is used interchangeably herein and means seeds, typically viable seeds, to which compositions of the invention may be applied. Vegetable seed as provided herein means seeds that are capable of germinating to at least conventional levels of germination typical of the relevant vegetable species under consideration. Thus a vegetable plant structure is one that may be grown for human or domesticated animal consumption. For the purposes of the present invention "vegetable plant structures" includes those structures such as seeds, bulbs and tubers, found in domestic vegetables. "Domestic vegetables" for the purposes of the present invention are ones which are recognised as such by the skilled addressee. Vegetable structures suitable for coating with compositions of the invention include those selected from members of the Crucifer family (cabbages, broccolis, cauliflowers, kales, Brussels sprouts, kohlrabis), onions, capsicums, tomatoes, cucurbits such as cucumbers, cantaloupes, summer squashes, pumpkins, butternut squashes, tropical pumpkins, calabazas, winter squashes, watermelons, lettuces, zucchinis (courgettes), aubergines, carrots, parsnips, potatoes such as white potato, swedes, turnips, sugar beet, celeriacs, Jerusalem artichokes, artichokes, bok choi, celery, Chinese cabbage, beans such as lima beans, green beans such as runner beans, haricot beans, French beans, broad beans, horse radish, leeks, musk melons, parsley, radish, spinach, sweet corn, sugar beet, beetroot for table consumption, peas and the like.

The organic carrier material is selected from organic materials that can be applied to vegetable plant structures such as seeds preferably as a dry powder wherein the powder particles are of a pre-determined volume mean diameter, or the powder particles are applied in liquid form, such as an oleaginous formulation or as an aqueous formulation.

Generally, the organic carrier material of use in the invention is present in the form of particles in a composition of the invention and possess a volume mean diameter of a certain size as defined herein. To obtain particles of organic materials of a volume mean diameter applicable for use in the invention, organic materials in the form of, for example, 1 to 5 kilogram blocks or tablets may be broken up or kibbled into small millimetre-sized pieces (such as from 2 mm-8 mm approximate diameter in size, for example from 4 mm to 6 mm) in a kibbling machine. The millimetre-sized pieces can then be passed through a comminuting means such as a standard mill, e.g. an Apex Comminuting mill, and milled or comminuted into particles having an approximate diameter in the range from 100 μm-500 μm, for example from 250 μm-300 μm. The micron-sized comminuted particles can then be passed through a micronising apparatus, such as an AFG micronising air mill to obtain particles of a desired VMD range, such as from 15 μm-20 μm, that is of use in the present invention. The skilled addressee will appreciate that such procedures for obtaining small particles are well known in the art. Preferably, dry powder compositions of the invention comprise composite particles having a volume mean diameter of ≥5 μm, for example of 8 μm, 9 μm, 10 μm, 11 μm, 12 μm, 13 μm, 14 μm, 15 μm up to 40 μm or any value therein between. As stated herein, the volume mean diameter of the composite particles is typically ≥10 μm or ≥12 μm and may lie in the range from 10 μm to 200 μm and may have a value that lies anywhere therein between, for example from ≥10 μm to 100 μm; or from Own to 40 μm; or from ≥10 μm to 30 μm or any desired volume mean diameter value in between. Preferably, dry powder compositions of the invention comprise particles having a volume mean diameter of ≥8 μm, for example of 8 μm, 9 μm, 9.7 μm, 10 μm, 11 μm, 12 μm, 13 μm, 14 μm, 15 μm and the like up to any volume mean diameter of choice, such as up to 200 μm or any volume mean diameter in between for example 40 μm or 30 μm. Particles of the invention that possess a volume mean diameter ≥10 μmare considered to be less of a thoracic hazard to humans and are not thought to be allergenic.

In liquid formulations, particles of a pre-determined volume mean diameter as herein described are suspended therein in a suspension formulation and applied to the seeds which are then dried using conventional drying procedures. Where the organic carrier material is applied to vegetable plant seeds in a dry powder form, the particles of the organic carrier material may have a volume mean diameter of any conventional size as herein described. To such dry powders, chemicals of use against arthropod pathogens such as insects, arachnids and if appropriate, their larvae, eggs, or pupae; chemicals of use against bacterial pathogens; and chemicals of use against fungal pathogens may be added prior to the coating of the oilseed. Additionally, beneficial live biological agents may be added to such dry powders of use in the present invention, the live biological agents being able to target bacterial pathogens of the vegetable plant and/or to target fungal pathogens of the vegetable plant. Spores of choice of beneficial live biological agents such as fungal conidia or hyphae or mycelia of fungi that do not form spores or conidia-like structures may be added to dry powders of use in the present invention. Suitable organic carrier materials of use in the invention are typically made up of organic materials such as waxes having a melting point of ≥50° C., more preferably of ≥60° C., and most preferably are made up of hard waxes having a melting point of ≥70° C.

Natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax and the like.

Synthetic waxes of use in the present invention include suitable waxes selected from paraffin wax, microcrystalline wax, Polyethylene waxes, Fischer-Tropsch waxes, substituted amide waxes, polymerized α-olefins and the like.

Mineral waxes of use in the invention include montan wax (e.g. Lumax® Bayer) ceresin wax, ozocerite, peat wax and the like.

Suitable organic carrier particles may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Such waxes typically display a high enthalpy of lattice energy during melt. Preferably the organic carrier material is carnauba wax which may be applied in liquid form, typically in the form of a suspension, or more preferably in powder form as discrete particles.

Additionally, the organic carrier particles of use in compositions of the invention may contain other components such as additives selected from UV blockers such as beta-carotene or p-amino benzoic acid, colouring agents such as optical brighteners and commercially available colouring agents such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled addressee will appreciate that the selection of such commonly included additives will be made depending on end purpose, and perceived need.

Liquid formulations of the invention may be formulated as an aqueous formulation or as an oleaginous formulation, depending on design. Aqueous formulations may include surfactants selected from commercially available surfactants such as Libsorb, Silwet L77, Tween 80, Torpedo II, Newmans T80, Fortune, Guard, Rhino, Biopower, and the like.

Oleaginous formulations, that is to say oil-based formulations, may contain any oil suitable for use in the present invention which may be selected from petroleum oils, such as paraffin oil, and vegetable oils such as rapeseed oil, soybean oil, sunflower oil, palm oil and the like. Oil formulations of use in the invention contain organic carrier particles as described herein and these in turn may be admixed with flow agents such as hydrophilic precipitated silicas, for example Sipernat 383 DS, Sipernat 320, EXP 4350, and Sipernat D-17 and the like. Such free-flowing agents may be dispersed in oils, for example, for anti-foaming purposes.

The skilled addressee will appreciate that where an aqueous or an oil formulation may be used to apply biological agents of use in the invention, the liquid element should be removed from the coated plant structure after coating is achieved, for example by drying off using conventional drying processes, leaving a seed coating composition in dry particulate form, wherein the seed coating composition is made up of the organic carrier as herein described and the at least one biological agent, also as herein described.

A biological agent for the purposes of the present invention is one that can be used to control the population of a plant pathogen of a vegetable plant, and may be selected from chemical fungicides, arthropodicides such as insecticides and acaricides, bactericides and from live biological agents that are able to control the population of one or more seed or soil borne pathogens of a vegetable plant structure, such as a seed, tap root, or other structure that is able to grow roots and/or shoots. Preferably, the population of the soil borne pathogen on or in the immediate vicinity of the vegetable plant structure is reduced either by the biological agent rendering it unable to reproduce and/or by killing it. Examples of biological agents of use in the present invention include chemicals for use on vegetable plant structures such as seeds selected from arthropodicides, such as insecticides and acaricides, fungicides and bactericides commonly employed in the art. Suitable examples of such chemicals include nicotinoid insecticides such as imidacloprid [(E)-1-(6-chloro-3-pyridylmethyl)-N-nitroimidazolidin-2-ylideneamine], methylcarbamate insecticides such as methiocarb [4-methylthio-3,5-xylyl methylcarbamate], oxime carbamate insecticides such as thiodicarb[(3EZ,12EZ)-3,7,9,13-tetramethyl-5,11-dioxa-2,8,14-trithia-4,7,9,12-tetraazapentadeca-3,12-diene-6,10-dione], and thiazole insecticides such as clothianicidin [(E)-1-(2-chloro-1,3-thiazol-5-ylmethyl)-3-methyl-2-nitroguanidine] (all used on sugar beet); suitable fungicides of use in the invention include aromatic fungicides such as dicloran[2,6-dichloro-4-nitroaniline](used on sweet potatoes), thiophanate fungicides such as Topsin M [thiophanate-methyl] (used on muskmelons, onions (dry and green), dithiocarbamate fungicides such as Thiram[tetramethylthiuram disulfide or bis(dimethylthiocarbamoyl) disulfide](used on beans, beetroot (beet), Cole crops, carrots, Chinese cabbage, Cucumbers, Aubergines (eggplants), mustard greens, turnip, lettuce, muskmelons, Okra, onions, peas, capsicums (peppers), pumpkins, radish, spinach, summer squash, sweet corn, tomatoes and watermelon); and mancozeb[manganese ethylenebis(dithiocarbamate) (polymeric) complex with zinc salt] (used on tomato), acylamino acid fungicides such as metalaxyl[methyl N-(methoxyacetyl)-N-(2,6-xylyl)-DL-alaninate] (used on beans, beet, carrots, cucumbers, peas, and sweet corn); and acyl amino acid fungicides such as mefenoxam[methyl N-(methoxyacetyl)-N-(2,6-xylyl)-D-alaninate] (used on beans, beet, broccoli, carrots, celery, Chinese cabbage, Cole crops, cucumbers, eggplants garlic, Mustard greens, turnip greens, horse radish, leeks, lettuce, musk melons, onions, garlic horseradish, parsley, parsnips, peas, peppers pumpkins/winter squash, radish, spinach, summer squash, sweet corn, sweet potatoes, tomatoes, and watermelon), phthalimide fungicides such as captan[N-(trichloromethylthio)cyclohex-4-ene-1,2-dicarboximide] used on beans, beets, broccoli, Cole crops, cucumbers, Mustard greens, Turnip greens, muskmelons, peas, peppers, pumpkins/winter squash, radish, spinach, tomato, summer squash, sweet corn, lentils, watermelon and white potatoes, conazole fungicides such as difenoconazole[3-chloro-4-[(2RS,4RS;2RS,4SR)-4-methyl-2-(1H-1,2,4-triazol-1-ylmethyl)-1,3-dioxolan-2-yl]phenyl 4-chlorophenyl ether], pyrrole fungicides such as fludioxinil [4-(2,2-difluoro-1,3-benzodioxol-4-yl)-1H-pyrrole-3-carbonitrile] (used on beans, beet, broccoli, carrots, celery, Chinese cabbage, Cole crops, cucumbers, eggplants garlic, Mustard greens, turnip greens, horse radish, leeks, lettuce, musk melons, okra (dry and green), onions, parsley, parsnips, peas, peppers pumpkins/winter squash, radish, spinach, summer squash, sweet corn, sweet potatoes, tomatoes, watermelon, and white potatoes), oxazole fungicides such as oxadixyl[2-methoxy-N-(2-oxo-1,3-oxazolidin-3-yl)acet-2', 6'-xylidide] (used on peas and beans) and EBDC fungicides such as the mixture Ethylenebisdithio-carbamate (used on potato seed tubers).

The skilled addressee will appreciate that compositions of the invention may also be added direct to the soil or growing medium into which plant structures as herein defined are to be planted. Such compositions may be added as powders and mixed with the soil or applied as liquid suspensions using conventional procedures.

Soil borne pathogens for the purposes of the present invention are ones that are able to colonise the vegetable plant structure, such as the seed cuticle and/or ones that populate the soil and which are capable of acting on vegetable plant structures, such as seeds. Such soil borne pathogens are typically bacteria and/or fungi. Examples of soil borne bacterial and fungal pathogens that attack vegetable plants include *Rhizoctonia* spp. (active against e.g. beans, cucurbits; *R. solani* active against *Brassica* spp. peas; lettuces, spinach, potato), *Pythium* spp. (active against e.g. beans, carrot, celery, *Brassica* spp., cucurbits, eggplant, lentils, peas, peppers, spinach, lettuce, potato and tomato), *Fusarium* spp. (active against e.g. beans, cucurbits, tomato, peas, potato), *Phytophthora* spp. (active against e.g. beans and lentils, cucurbits, tomato, spinach, potato; *P. megasperma* active against *Brassica* spp.), *Verticillium* spp. such as *V. albo-atrum* and *V. dahliae* (active against *Brassica* spp., tomato, potato), *Sclerotium* spp. (active against e.g. beans), *Agrobacterium tumefaciens* (active against *Brassica* and *Raphunus* spp.), *Phoma* spp. (active against peas) such as *Phoma lingam* (active against *Brassica* spp.), *Erwinia* spp. (active against cucurbits, tomato, lettuces, potato), *Pseudomonas* spp. (active against cucurbits, tomato, spinach, beans, potato), *Alternaria* spp. (active against cucurbits, lettuces, peas, tomato, potato), *Penicillium* spp. (active against cucurbits), *Streptomyces* spp. (active against potato), and the like.

According to a further aspect of the invention there is provided use of organic carrier particles of wax in the manufacture of a coating composition as defined herein that includes a biological agent as defined herein above. In a preferment of this aspect of the invention, the coating composition is a seed coating composition. In a further preferment of this aspect of the invention the coating composition is a storage organ coating composition wherein the storage organ is selected from tubers, tuberous roots, corms, bulbs and rhizomes. The organic carrier particles are selected from natural waxes, synthetic waxes, and mineral waxes having a melting point of ≥50° C., more preferably of ≥60° C., and most preferably are made up of hard waxes having a melting point of ≥70° C. Suitable waxes of use in this aspect of the invention may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the seed coating that is employed in this aspect of the invention includes carnauba wax as the organic carrier. Preferably, in this aspect of the invention, the organic carrier particles have a mean volume diameter ≥5 μm, such as in the range ≥8 μm to 200 μm, as herein described.

In a third aspect of the invention there is provided use of wax as an organic carrier in particulate form in a vegetable structure coating composition as described herein. The organic carrier particles in this aspect of the invention are selected from natural waxes, synthetic waxes, and mineral waxes having a melting point of ≥50° C., more preferably of ≥60° C., and most preferably are made up of hard waxes having a melting point of ≥70° C. Suitable organic carrier particles of use in this aspect of the invention may be selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the wax carrier particles of use in this aspect of the invention comprise organic carrier particles of carnauba wax. Preferably still, the organic carrier particles of use in this aspect of the invention have a mean volume diameter ≥8 μm, such as in the range of ≥10 μm to 200 μm.

In a fourth aspect of the invention there is provided a method of manufacturing a vegetable plant structure coating, for example a seed coating composition as herein described that comprises
1) selecting an organic carrier material wherein the carrier material is selected from waxes having a melting point of ≥50° Centigrade;
2) comminuting said organic carrier material into particles of a desired mean volume diameter ≥5 μm, such as in the range 8 μm to 200 μm; and
3) adding biological agent to the product particles of step 2).

The biological agent of use in this aspect of the invention is selected from an insecticide or an acaricide or a mixture thereof, or a chemical fungicide or a fungus species and/or a bacterium species or a mixture of one or more thereof.

Examples of live biological agents (also known as biocontrol organisms or biocontrol agents) that are commonly referred to in the art as "biological antagonists" that may be used in coating compositions of the present invention include *Pseudomonas* spp., *Trichoderma* spp. such as *T. viride* (but not for use on onions) (in seed dressings is active against *Rhizoctonia solani, Macrophomina phaseolina* and *Fusarium* spp.), *Streptomyces* spp., such as *Streptomyces lydicus* (available from Natural Industries Inc., Houston, Tex., USA), *Ampelomyces quisqualis* isolate M-10 (available from Ecogen Inc, Langhorne, USA), *Bacillus* spp., such as *Bacillus subtilis* GB03*, B. lichenformis*, and *B. megaterium* (all available from Growth Products, White Plains, USA), *Coniothyrium minitans* (available from Prophyta Biologischer Pflanzenschutz GmbH, Germany), *Agrobacterium radiobacter* Strain 84 (available from AgbioChem Inc, Florida, USA), *Erwinia amylovora* HrpN harpin protein (available from Eden Bioscience Corp., Bothell Wash., USA), *Streptomyces griseoviridis* strain K61 (available from Kemira Agro Oy, Helsinki, Finland), *Agrobacterium radiobacter* K1026 (available from Bio-care Technology, Australia), *Gliocladium catenulatum* (available from Kemira Agro Oy, Helsinki, Finland), *Trichoderma harzianium* Rifai strain KRL-AG2 (T-22) (available from Bioworks Inc, Geneva, USA), and *Gliocladium virens* (aka *Trichoderma virens*) GL-21 (available from Certis Inc., Columbia, USA), *Bacillus subtilis* GB03 (used on peas and sweet corn), and *Bacillus pumilus* GB34 (used on peas).

Suitable fungicides are known for use in seed treatments on vegetable plant structures such as vegetable seeds. Suitable examples of such chemicals include the insecticides such as imidacloprid [(E)-1-(6-chloro-3-pyridylmethyl)-N-nitroimidazolidin-2-ylideneaminel], methiocarb[4-methylthio-3,5-xylyl methylcarbamate], thiodicarb[(3EZ,12EZ)-3,7,9,13-tetramethyl-5,11-dioxa-2,8,14-trithia-4,7,9,12-tetraazapentadeca-3,12-diene-6,10-dione], and clothianicidin [(E)-1-(2-chloro-1,3-thiazol-5-ylmethyl)-3-methyl-2-nitroguanidine] (all used on sugar beet); fungicides such as dicloran[2,6-dichloro-4-nitroaniline](used on sweet potatoes), mefenoxam[methyl N-(methoxyacetyl)-N-(2,6-xylyl)-D-alaninate](used on garlic, horseradish, lettuce, Topsin M [thiophanate-methyl](used on muskmelons, onions (dry and green), Thiram[tetramethylthiuram disulfide or bis(dimethylthiocarbamoyl)disulfide](used on beans, beetroot (beet), broccoli, carrots, Chinese cabbage, Cucumbers, Aubergines (eggplants), mustard greens, turnip, lettuce, muskmelons, Okra, onions, peas, capsicums (peppers), pumpkins, radish, spinach, summer squash, sweet corn, tomatoes and watermelon), metalaxyl[methyl N-(methoxyacetyl)-N-(2,6-xylyl)-DL-alaninate](used on beans, beet, carrots, cucumbers, peas, and sweet corn), mefenoxam[methyl N-(methoxyacetyl)-N-(2,6-xylyl)-D-alaninate] (used on beans, beet, broccoli, carrots, celery, Chinese cabbage, Cole crops, cucumbers, eggplants garlic, Mustard greens, turnip greens, horse radish, leeks, lettuce, musk melons onions, parsley, parsnips, peas, peppers pumpkins/winter squash, radish, spinach, summer squash, sweet corn, sweet potatoes, tomatoes, and watermelon), captan[N-(trichloromethylthio)cyclohex-4-ene-1,2-dicarboximide] used on beans, beets, broccoli, Cole crops, cucumbers, Mustard greens, Turnip greens, muskmelons, peas, peppers, pumpkins/winter squash, radish, spinach, summer squash, sweet corn, watermelon and white potatoes, difenoconazole[3-chloro-4-[(2RS,4RS;2RS,4SR)-4-methyl-2-(1H-1,2,4-triazol-1-ylmethyl)-1,3-dioxolan-2-yl]phenyl 4-chlorophenyl ether] and mefenoxam[methyl N-(methoxyacetyl)-N-(2,6-xylyl)-D-alaninate] (used on sweet corn), *Bacillus subtilis* GB03 (used on peas and sweet corn), fludioxinil[4-(2,2-difluoro-1,3-benzodioxol-4-yl)-1H-pyrrole-3-carbonitrile] (used on beans, beet, broccoli, carrots, celery, Chinese cabbage, Cole crops, cucumbers, eggplants garlic, Mustard greens, turnip greens, horse radish, leeks, lettuce, musk melons, okra (dry and green), onions, parsley, parsnips, peas, peppers pumpkins/winter squash, radish, spinach, summer squash, sweet corn, sweet potatoes, tomatoes, watermelon, and white potatoes), Ethylenebisdithiocarbamates (EBDC) (used on potato seed tubers), *Bacillus pumilus* GB34 (used on peas).

Suitable examples of such chemicals further include the insecticides such as imidacloprid [(E)-1-(6-chloro-3-pyridylmethyl)-N-nitroimidazolidin-2-ylideneamine], methiocarb[4-methylthio-3,5-xylyl methylcarbamate], thiodicarb[(3EZ,12EZ)-3,7,9,13-tetramethyl-5,11-dioxa-2,8,14-trithia-4,7,9,12-tetraazapentadeca-3,12-diene-6,10-dione], and clothianicidin [(E)-1-(2-chloro-1,3-thiazol-5-ylmethyl)-3-methyl-2-nitroguanidine] (all used on sugar beet) and the like.

The organic carrier material in this aspect of the invention may be selected from waxes such as from those waxes as hereinbefore described. Suitable waxes may be selected from waxes such as carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the wax carrier particles of use in this aspect of the invention comprise dry particles of carnauba wax. Preferably, the selected carrier material is carnauba wax.

In a further aspect of the invention, there is provided a vegetable plant structure coating composition, such as a seed coating composition produced by the method as described herein.

In a further aspect of the invention there is provided a coating composition as described herein for use on vegetable plant structures, such as seeds.

In a further aspect of the invention there is provided a method of coating a vegetable plant structure, such as a vegetable seed with a coating composition that comprises an organic carrier material and a biological antagonist to one or more fungal pathogens, bacterial pathogens and arthropod pathogens so as to limit damage by the said pathogens to the said vegetable plant structure, such as a vegetable seed, the method comprising adding a biological antagonist to an organic carrier material wherein the organic carrier material is in dry particulate form, mixing the two components together and applying the resulting composition in dry particulate form to vegetable plant structures, such as vegetable seeds. Thus, the seed coating composition is applied in dry particulate form. Naturally, the skilled addressee will appreciate that the organic carrier material may also contain added pigments, plasticisers and other minor components as herein described. In an alternative, the seed coating may be applied in liquid form as herein described and then the seeds dried, leaving a coating composition that is in dry particulate form when on the seed. However, it is preferred that the coating composition is applied in dry, particulate form for ease of application and production costs are kept low. The organic carrier material in this aspect of the invention may be selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax, and rice bran wax or a mixture of two or more thereof. Preferably, the organic carrier material is carnauba wax in dry particulate form.

The treatment composition in this aspect of the invention includes one or more biological agents selected from chemical arthropodicides such as insecticides and acaricides, fungicides, bactericides and live biological agents as herein before described.

There now follow examples that illustrate the invention. It is to be understood that the examples are not to be construed as limiting the invention in any way.

FIG. 1: Spore loadings of *Trichoderma* on radish

EXAMPLES SECTION

Control of *Pseudomonas syringae* pv *syringae* [United Kingdom National Culture Collection (UKNCC)] on common bean (*Phaseolus vulgaris*) by means of seed treatments.

Using the antagonists *Trichoderma harzianum*, *Pseudomonas fluorescens* and *Bacillus subtilis* [United Kingdom National Culture Collection (UKNCC)]
Bacterial Brown Spot
Symptoms

*Pseudomonas syringae* pv. *syringae* can cause diseases on several kinds of plants, but only a unique form of this bacterium causes that known as bacterial brown spot. These bacteria can grow on the surface of some plants, including snap and dry beans, without causing disease. Bacteria that exist this way are called epiphytes. Bacterial brown spot on beans often occurs after large epiphytic populations of the bacteria develop. Since severe infection may not develop until after a major rainstorm, an absence of symptoms does not mean that the bacteria are not present.

The initial foliar symptom of bacterial brown spot is small water-soaked spots that develop into distinctive necrotic brown spots about 3-8 mm in diameter, often with a narrow, diffuse yellow margin. These lesions may enlarge, coalesce, and fall out giving the leaves a tattered appearance. Sunken brown spots can form on the pods. If infection occurs early in pod development, the pod may become bent or twisted at the infection site.

Disadvantages of Conventional Seed Treatment
i) Limited dose capacity—The amount of pesticide that can be applied is limited by how much will actually stick to the
ii) Limited duration of protection—The duration is often short due to the relatively small amount of biological agent (e.g. chemical) applied to the seed, dilution of the biological agent as the plant grows, and breakdown of the biological agent.
iii) Limited shelf life of treated seed—Producing excess treated seed is undesirable because the shelf life of treated seed may be limited.

All three of these limitations may be overcome or significantly reduced through the inclusion of carnauba wax particles as a carrier for a biological agent, in this case dormant microorganisms that are applied to seeds. Under favourable conditions, the microorganisms grow and colonize the exterior of the developing seed or seedling. Biological agents may help in reducing seed decay, seedling diseases, or root rot.

The following tests are performed to examine the potential effect of the inclusion of carnauba wax particles.
Phase One—Isolate Cultures
1. Culture Maintenance Records are kept with each isolate sub-culture being assigned an accession number. All plates and slides relating to that sub-culture are labelled with an accession number.

In addition, permanent lactophenol (LP) mounted slides are made from each of the original cultures and filed for reference purposes.

No more than three generations of sub-culture occur before passaging through a living host and re-isolating in order to maintain the fitness of the organism.

Sub-cultures are stored for future use on Potato Dextrose Agar (PDA) at 4° C.

Each isolate is assigned an accession number and sub-cultures are labelled with that number.

DNA is extracted for identity verifications and stored at −20° C. A reference sample of the pure culture is stored on glycerol at −20° C. Upon completion of the experiment DNA identification of the culture is repeated to confirm that the organism has not mutated during the course of the work.
2. Culturing of the Causal Agent Isolation of pathogenic bacteria from diseased tissue into pure culture is one of the standard techniques in identifying and describing a disease. It is an essential step in proving the pathogenicity of previously un-encountered organisms.
Techniques Commonly Involve:
a. Surface-sterilisation treatment
b. Plating (possibly on selective medium) of samples of diseased tissue, with appropriate precautions.
c. Sub-culturing to get pure cultures.
3. Purification of Cultures Small disinfected root pieces of an artificially inoculated plant are cultured on water agar. The bacterial colonies that appear most frequently are likely the target pathogen. Several saprophytes may also be present in infected plant tissues and they may grow into the medium with the principal pathogen. Routine surface-sterilisation consists of wiping the tissue with (or immersing in) 0.1% solution of sodium hypochlorite (NaOCl—sometimes referred to as "NaClO") followed by rinsing with sterile distilled water. To obtain a pure culture of the pathogen, a small sample is taken from the growing edge of a colony with a flamed loop or scalpel and streaked over the surface of a pre-poured plate of PDA. The inclusion of cycloheximide (an anti-fungal agent capable of supressing saprophytic fungal growth) at 30 mg/l reduces the risk of bacterial contamination. As the streak progresses over the agar, spores are separated until single spores are obtained from which separate colonies will grow.

Repeat this procedure until pure cultures are obtained.

4. Single Spore Isolation

Single spore isolations are important to investigate pathogenic variability. An inoculum of spores is placed in a tube containing 10 ml of sterile water. This spore suspension is streaked along a marked line on the surface of a thin tap water agar medium, and incubated at 22° C. After 24 hr incubation, select germinated spores using a stereoscopic microscope and transferred one spore at a time to another agar plate.

5. Slide Preparation for Microscopic Examination and Reference

Identification of the pathogen, rather than the disease, requires microscopic examination of infected tissue.

Place a drop of water into the wax circle that has been created on the slide. Using a sterilized and cooled inoculation loop, obtain a very small sample of a bacterial colony. Gently mix the bacteria into the water drop. Heat fix the bacterial sample to kill the bacteria, firmly affix the smear to the microscope slide and allow the sample to more readily take up the stain. First let the bacterial sample air dry. Then pass the dried slide through the flame of a Bunsen burner 3 or 4 times, smear side facing up. Once the slide is heat fixed, it is then stained.

*P. syringae* pv. *syringae* is a Gram-Negative bacterium. Gram-bacteria stain pink due to the location of cell wall peptidoglycan and an external LPS membrane. The cell walls of Gram-bacteria are more chemically complex and thinner than Gram-positive cell walls. Peptidoglycan makes up only 5-20% of the Gram-negative cell wall, and is not the outermost layer, but lies between the plasma membrane and an outer membrane. This outer membrane is similar to the plasma membrane, but is less permeable and composed of lipopolysaccharides (LPS), a harmful substance classified as an endotoxin.

The Gram Staining procedure goes as follows:
1. Flood the slide with Crystal Violet (the primary stain).
2. After 1 minute, rinse the slide with water.
3. Flood the slide with Iodine (Iodine is a mordant that binds the Crystal violet to the Gram+cell wall.)
4. After 1 minute, rinse the slide with water.
5. Flood the slide with Acetone Alcohol. (Alcohol is a decolourizer that will remove the stain from the Gram-negative cells.)
6. After 10 or 15 seconds, rinse the slide with water. (Do not leave the decolourizer on too long or it may remove stain from the Gram-positive cells as well.)
7. Flood slide with Safrinin (the counterstain).
8. After 1 minute, rinse the slide with water.
9. Gently blot the slide dry. It is now ready to be viewed under oil immersion (1000×TM) with a bright-field compound microscope.

The Gram-cells will appear pink, having retained the counterstain after the primary stain was removed by the decolourizer.

10. Growth and Media

Sub-cultures are assessed for growth and germination at a range of temperatures, 15° C., 20° C. and 25° C. A range of media is examined for suitability. Whilst PDA is generally suitable for most fungal species it has been found that use of a low nutrient agar, such as tap-water agar, reduce prolific growth and can encourage sporulation. Therefore PDA, tap-water agar, and a selective media from literature, modified Tween medium B (McGuire, R.G. 1986 *Plant Disease* 70: 887) are included within the assessment trials A 5 mm diameter disk is cut from the margin of an actively growing culture using a flamed cork borer. This is placed upside down in the centre of the pre-poured media plates. Five replicates are made for each media type and temperature (45 plates in total). Complete randomisation is applied to plates in each incubator. Plates are observed until one culture succeeds in completely covering the plate in any one media. At this point the following measurements are taken: colony diameter, colour and margin. In addition, the level of sporulation is recorded.

Five 5 mm disks are cut from each plate using a flamed cork borer and suspended in 20 ml of distilled water (+0.05% Tween 20®). The sample is then sonicated for 2 minutes to release the spores and then vortexed to aid the formation of a uniform spore suspension. Samples are assessed for spore concentration using an Improved Neubauer haemocytometer using standard counting methodology.

The mean for each media type is calculated and ANOVA is applied to examine the results for significant differences.

Phase Two—In Vitro Studies:

1. Screen Microorganisms and Carnauba Wax to Determine Interactions

In order to explain effects observed the microorganisms, pathogens and antagonists, are screened against carnauba wax to identify any carrier only effect. This enables the determination of treatment effect as well as any synergy occurring as a result of the use of using an antagonist with carnauba wax particles.

a. Plates of appropriate media are used based on the findings of the experiment above. Air-milled carnauba wax is sterilised using the autoclave and then ground using a twin blade mill, producing particles with an approximate VMD of 130 μm. The sterilised media is then cooled to 50° C. (molten stage). The carnauba wax is then incorporated into the media. Two concentrations of carnauba wax are tested; 1 g/l and 10 g/l. A 5 mm diameter disk is cut from the margin of an actively growing culture using a flamed cork borer. This is placed upside down in the centre of the pre-poured media/carnauba wax plates. Five replicates are made for each concentration and incubated at the optimum temperature for growth/sporulation (as determined in previous experiment). Growth rates and characteristics are compared to the controls using data from the Growth and Media experiment above.

Differences are analysed using ANOVA.

b. Disks of the pathogen and antagonists are dusted with different carnauba wax treatments and put on appropriate media. The carnauba wax particles need to be free of microorganisms to be able to carry out this experiment. Growth of treated and untreated organisms are compare 2. d. Investigate Antagonist Action Against Pathogens i. Effect of Antagonists on Viability of *P. Syringae* Pv. *Syringae* (In Vitro Assay I)

All antagonistic isolates are tested in a dual culture assay against pathogenic bacteria on PDA or alternative pre-defined media. Agar plugs of *P. syringae* pv. *syringae* and the antagonist isolate to be tested are arranged 7 cm apart on 9 cm agar plates. Inhibition zones and zones of overlapping are assessed after 7 days incubation at 13.5° C., 18° C. and 22.58° C. Where an antagonist overgrows the *P. syringae* pv. *syringae*, the zone of interaction between both is investigated microscopically (100×). Furthermore, the viability of *P. syringae* pv. *syringae* in the region of interaction is tested by transfer of vegetative discs onto water agar plates 5 days after first contact. Each experiment is repeated three times with three samples per replicate.

ii. Effect of Antagonists on Germination of *P. Syringae* Pv. *Syringae* Produced in Vitro (In Vitro Assay II)

*P. syringae* pv. *syringae* spores of uniform size are placed on a 6 day old culture (PDA, 20° C.) of the antagonist. After incubation for 14, 28 and 35 days at 20° C., eight spores per replicate (three replicates per antagonist) are transferred from the agar plate onto water agar. Growth from these spores will be assessed under a light microscope (100×).

3. Confirmation of Pathogenicity

Steps to perform Koch's postulates (Koch 1890, criteria designed to establish a causal relationship between a causative microbe and a disease)

a) Describe the symptoms expressed by the diseased crop plants.
b) Isolate the suspected pathogen—the same cultures should be isolated from plants with similar symptoms.
c) Obtain a pure culture and use it to inoculate healthy plant material.
d) Observe the symptoms expressed by the inoculated plants—symptoms should be the same as those observed originally in the crop plants.
e) Re-isolate the pathogen from the newly diseased material. The culture should be the same as the original purified culture.

i. Indirect Application—Plant

Using healthy plants—soil can be inoculated directly using a spore suspension made from a pure agar culture or from a culture grown in flasks. A fungal spore or bacterial suspension can be added post-emergence so that the root system is drenched by the suspension. Plants are then observed over 7 days and symptoms recorded. Koch's Postulates are applied in order to confirm that the symptoms relate to the inoculated pathogen.

ii. Direct Application—Seed

Inoculum for preparing spore suspensions will be grown on water agar containing sterile seeds. Fungal spores and hyphae or bacterial spore and vegetative growth are scraped from the colony and transfer to sterile water. This spore suspension is applied to seeds and mixed to ensure a uniform distribution. Seeds are then:

Placed on moist filter paper and incubated at optimum growth temperature for 5 days.
sown in heat sterilised potting compost and incubated in a propagator at optimum growth temperature for 7 days Symptom expression and germination is recorded for both sets of experiments and Koch's postulates applied 4. Carnauba Wax/Antagonist Co-Location Analysis A dry powder formulation of spores is produced using a spore separator. Moisture content of the formulation is reduced to below 5% using a dehumidifier and silica beads. Spore concentration is determined using a Neubauer haemocytometer and standardised counting methodology.

Steps in Air Milling in Boyes Micronisation Process (for carnauba wax particles with a VMD of approx. 15 μm and 75 μm, respectively)

1. 2 kg carnauba wax blocks are first kibbled into approximately 4 to 6 mm pieces in a KT Handling Ltd Model 04 kibbler (serial no. 729/C) following the manufacturer's instructions.
2. The kibbled pieces are then passed through an Apex Construction Ltd Model 314.2 Comminuting Mill (serial no. A21306) and reduced further in size to a range of 250 to 300 um.
3. The comminuted particles are then passed through a Hosokawa Micron Ltd Alpine 100AFG jet mill (serial no. 168092) following the manufacturer's instructions, setting the mill at a suitable speed (a speed of 8000 rpm for particles having a VMD of 15 μm or at a speed of 2500 rpm for particles having a VMD of 75 μm), with a positive system pressure of 0.03 bar.
4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of 15 um or 75 μm as required.

Entostat was combined with vegetable seed at three loadings (see below).

Two sizes of carnauba wax particle having VMDs of 15 μm and 75 μm, respectively are examined in combination with the spore formulation at two different ratios (1:3, 2:2). Samples of the carnauba wax/spore mixture are analysed using electron photomicroscopy to determine the co-location effect. Any variation observed is recorded.

In addition, both sizes of carnauba wax referred to, are mixed with a homogenised sample of mycelium and examined as described above.

5. Carnauba Wax Particle Loading

Carnauba wax particle adhesion to seeds is approximated through the use of photomicroscopy (qualitative) and fluorometric analysis (quantitative). Two sizes of carnauba wax particles (with 1% glo-brite) are used having a VMD of 15 μm and 75 μm, respectively. Three combinations: Two ratios of carnauba wax/spore formulation, and a vehicle control (carnauba wax only), makes a total of six treatments. Treatments are applied to 10 g of seed and replicated three times. Three subsamples are taken from each replicate and the mean used in analysis.

For fluorometric analysis three 1 g samples are each added to 5 ml of ethanol and sonicated to aid the release of the carnauba wax particles from the seeds. Samples are analysed using a Perkin Elmer L55 Fluorometer (Perkin Elmer, Ma, USA). Statistical analysis of variation between treatments is performed using ANOVA.

Seed size and architecture varies greatly between crop species and this influences application rates and method. A homogeneous mix is attained through tumbling seed and carnauba wax formulation in a cylinder, adapted to produce lateral mixing/tumbling through the inclusion of angled interior vanes, placed on a Wheaton roller for 5 minutes.

Phase Three—In Vivo:

*P. syringae* pv. *syringae*, together with the most successful antagonist model is used in a series of in vivo experiments. The basic design is a split-plot experiment with temperature being the main plot factor (15° C., 20° C. and 25° C.) and carnauba wax/antagonist ratio (2 treatments:2× spore) being the sub-plot. Four homogeneous mixes of each treatment are prepared using the method described above and these represent the replicates.

Treatments:
1) Application rate 1—7.5×10$^6$ conidia kg$^{-1}$
2) Application rate 2—7.5×10$^8$ conidia kg$^{-1}$
3) Control 1—Vehicle control (Carnauba wax only)
4) Control 2—no treatment
Mixes (true replicates): A, B, C, D
Subsamples of each mix: α, β
Mixes and treatments are arranged according to a Randomised Block design.

Pot Studies

Each temperature (growth chamber) contains 60 plant pots.

Treated seed is sown in accordance with supplier's recommendation. Soil/compost (1:1 John Innes No. 2 and peat compost) is heat sterilised prior to inoculation with 10 ml of *P. syringae* pv. *syringae* spore suspension and thoroughly mixed before sowing.

Plants are placed in the growth chambers for a period of 21 days with observations of symptom expression made every 48 hours post emergence. Water is applied through capillary matting twice daily.

After 21 days plants are removed from their pots and the following assessment measurements taken:

% germination
% pre-emergence damping off
% post-emergence damping off
Root weight
Shoot weight In addition, symptom expression is assessed based on a damage scale (FAO 1971). Means of the measurements taken from the subsamples α, β, γ are compared for each treatment using ANOVA.

Samples are taken from 5 plants exhibiting symptoms and Koch's Postulates applied to confirm the causal organism (by comparison to the reference slide of the master culture).

The experiment is repeated.

Second Example

Control of *Rhizoctonia solani* [United Kingdom National Culture Collection (UKNCC)] on common bean (*Phaseolus vulgaris*) by means of seed treatments using cymoxanil.

Experimental Design—as Pot Study in Example 1, Above

Carnauba wax is melted using copper pans. During cooling cymoxanil is added at 1% of the mass of the carnauba. This mixture is allowed to solidify before chipping and processing through a mill using the methodology described in example 1 to produce particles with a VMD of 25 μm.

Treatments for the Pot Study—

Control 1—Vehicle control (Carnauba wax only)

Control 2—no treatment

Treatment 1—1% cymoxanil carnauba wax at 5 g per kg of seed

Treatment 2—1% cymoxanil carnauba wax at 1.6 per kg of seed

Assessment and analysis as with previous Pot Study

Third Example

Relating to:

Control of *Agriotes* spp. (Coleoptera: Elateridae) also known as wireworms, this is the larval form of the click beetle) by means of seed treatments using thiamethoxam.

Early-season wireworm damage consists of hollowed-out seeds where larvae have entered during germination. Seedling plants also can be injured or killed by larvae tunnelling into the plant below the soil line. Occasionally, wireworms bore into the stalks of larger plants and tunnel in a few inches, but the damage is not significant.

Experimental Design—as for Pot Study of Example 1, Above

Carnauba wax is melted using copper pans. During cooling thiamethoxam is added at 1% of the mass of the carnauba. This mixture is allowed to solidify before chipping and processing through a mill (using the methodology of example 1) to produce particles with a VMD of 25 μm.

Treatments for the Pot Study—

Control 1—Vehicle control (Carnauba wax only)

Control 2—no treatment

Treatment 1—1% thiamethoxam carnauba wax at 4.2 g per kg of seed

Treatment 2—1% thiamethoxam carnauba wax at 1.3 g per kg of seed

Empty pots are lined with a nylon mesh screening material before filling with potting soil. A wire frame is constructed and the nylon meshed tied off over the frame to provide a caged experimental arena designed so that the insect cannot escape the treated area.

Seeds are allowed to germinate for three days before adding five $3^{rd}$ instar larvae to the soil surface of each pot before resealing the mesh cage.

Observations are made over 21 days.

Plants are assessed for:

% germination
Damage
Root weight
Shoot weight

The procedures detailed within Example One are followed to examine the antagonistic effect of *Trichoderma harzianum* [United Kingdom National Culture Collection (UKNCC)], *Pseudomonas fluorescens* [UKNCC] and *Bacillus subtilis* [UKNCC] on *Pseudomonas syringae*

*P. syringae*, a bacterial pathogen of Pepper (*Capsicum* sp.).

The procedures detailed within Example One are followed to examine the antagonistic effect of *Trichoderma harzianum* [United Kingdom National Culture Collection (UKNCC)], *Pseudomonas fluorescens* [UKNCC] and *Bacillus subtilis* [UKNCC] on *Pseudomonas syringae*, a bacterial pathogen of Pea (*Pisum sativum*).

The procedures detailed within Example One are followed to examine the antagonistic effect of *Trichoderma harzianum* [United Kingdom National Culture Collection (UKNCC)], *Pseudomonas fluorescens* [UKNCC] and *Bacillus subtilis* [UKNCC] on *Pseudomonas syringae*

*P. syringae*, a bacterial pathogen of Summer Squash (*Cucurbita pepo*).

The procedures detailed within Example Two are followed to examine the effect of metalaxyl on *Pythium* sp., a fungal pathogen of Pepper (*Capsicum* sp.).

The procedures detailed within Example Two are followed to examine the effect of triticonazole on *Rhizoctonia* sp., a fungal pathogen of Summer Squash (*Cucurbita pepo*).

The procedures detailed within Example Two are followed to examine the effect of metalaxyl on *Aphanomyces* euteiches, a fungal pathogen of Pea (*Pisum sativum*).

The procedures detailed within Example Three are followed to examine the effect of thiamethoxam on wireworms (*Conoderus vespertinus*), an insect pest of Pepper (*Capsicum* sp.).

The procedures detailed within Example Three are followed to examine the effect of imidacloprid on Southern Corn Rootworm, (*Diabrotica undecimpunctata* howardi), an insect pest of Summer Squash (*Cucurbita pepo*).

The procedures detailed within Example Three are followed to examine the effect of thiamethoxam on Granulate Cutworm, *Feltia subterranea*, an insect pest of Pea (*Pisum sativum*).

Suppression of Causal Agents of Fungal Disease in Radish (*Raphanus sativus*) Using a Seed Coating Comprised of *Trichoderma* sp. and Carnauba Wax Particles The potential for *Trichoderma* sp. (Ascomycota) as a biocontrol agent in the defence against plant pathogens is known.

*Trichoderma* hyphae are capable of penetrating the hyphae of other fungi and extracting nutrients from within, resulting in the suppression and eventual death of the host. *Trichoderma* exhibits rapid mycelial growth and is capable of out-competing other fungi for nutrients.

There are several commercially available formulations of *Trichoderma* marketed as crop protection products. These are commonly supplied as a wettable powder formulation and applied to the area of cultivation as a drench. The disadvantage of this form of application is that it is necessary to treat the entire cultivation area, whereas it is the region immediately surrounding the seed or plant that requires the treatment. The larger the number of conidia delivered to this area the greater the level of control they are able to impart. Therefore a targeted application system able to deliver sufficient conidia to the required area offers a distinct advantage in the use of *Trichoderma* over conventional applications.

Experimental Aim: To Assess the Potential Use of Entostat as a Seed-Coating Technology for the Delivery of Beneficial Microbes Methods Steps in Air Milling in Boyes Micronisation Process (for carnauba wax particles with a VMD of approx. 10 µm)

1. 2 kg carnauba wax blocks are first kibbled into approximately 4 to 6 mm pieces in a KT Handling Ltd Model 04 kibbler (serial no. 729/C) following the manufacturer's instructions.
2. The kibbled pieces are then passed through an Apex Construction Ltd Model 314.2 Comminuting Mill (serial no. A21306) and reduced further in size to a range of 250 to 300 um.
3. The comminuted particles are then passed through a Hosokawa Micron Ltd Alpine 100AFG jet mill (serial no. 168092) following the manufacturer's instructions, setting the mill at a speed of 12,500 rpm for particles having a VMD of about 10 µm), with a positive system pressure of 0.03 bar.
4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of 9.7 µm.

Entostat was combined with oilseed at three loadings (see below).

1. Baseline data: seed coating techniques
1.1. Seed Coating. *Trichoderma harzianum* (containing $7.75 \times 10^9$ colony forming units $g^{-1}$ Sylvan Bio, Loches, France) with a germination percentage of 95% was applied to radish (var. Cherry Belle) supplied by Herbiseed, (Twyford, UK) using carnauba wax particles with a VMD of 9.7 µm. A target loading was set at $10^5$ conidia per seed based on information obtained from literature.

Carnauba particles were mixed with the dry conidia powder at different ratios and applied 0.01 g (0.2% by mass) directly to dry seed, 5 g of seeds per concentration. For each concentration, four batches of 10 seeds were used for evaluation of conidia loading.

Conidia to carnauba ratios used were:

100% Conidia, 50% Conidia, 25% Conidia and 9% Conidia with the remainder in each case being made up of carnauba wax particles.

1.2. Enumeration. Direct enumeration to determine conidia loading of seeds was done through the use of a haemocytometer (Improved Neubauer, Hawksley, Lancing, UK). Inoculum: Preparation of suspension.

Propagules are usually formulated in a water carrier, although those with hydrophobic cell walls (such as *Trichoderma*) are not readily suspended in water. To uniformly suspend hydrophobic propagules in water it is necessary to sonicate and/or use mechanical suspension methods. Mechanical suspension of propagules using micropestles provides good suspension of conidia in water without causing damage to cells. A surfactant may also facilitate suspension of propagules (Tween20 at 0.05%). To suspend hydrophobic conidia, harvested conidia are placed in a 1.5 ml microcentrifuge tube, ≈0.5 ml of sterile water is added to the tube, the micropestle is inserted into the tube, and the conidial mass is gently agitated with the micropestle by hand. The micropestle is the attached to the motor (e.g. Kontes, Argos pellet pestle motor) and the suspension is vigorously agitated while moving the pestle in and up and down, and side to side motion, circa. 30 seconds. Since the haemocytometer method does not distinguish between viable and non-viable propagules, it is necessary to determine spore viability so that doses can be prepared on the basis of viable propagules. Seed washes and enumeration of *Trichoderma* loadings were done on 4 batches of seeds per treatment. Inoculum was washed from seeds by placing into 1 ml sterile 0.05% Tween$^{20}$ (or substitute—similar non-ionic surfactant/dispersal agent) in a Eppendorf tube and vortexing for 30 seconds to remove conidia from the seed surface. Samples were then sonicated for two minutes to break up any conidial clumping. Counts obtained were used to calculate the mean conidia loading of seed coated with the various treatments. Results obtained using 100% conidia powder were used as a benchmark and the conidia/carnauba combination powders compared against it as a determination of efficiency of loading.

Confirmation of conidial viability was achieved by dilution plating on *Trichoderma* Specific Media (TSM) (see below). A dilution series was set up and duplicate plates inoculated from the series. Colony Forming Units (CFU) counts were made after 7 days, allowing inoculum levels on seeds to be quantified. In addition, fresh, unused conidia were plated to provide a comparison of before and after seed application.

Germination percentage was also measured. A satisfactory density of conidia was obtained by spreading approximately $10^6$ conidia in 100 µl on the media in a 9 cm petri dish. Conidia were incubated in the dark at 25° C. for five days, and the area to be observed was then fixed using lactophenol. Phase contrast microscopy using an inverted compound microscope enabled sufficient examination of the conidia.

Conidia were considered viable if germtube lengths were two times the diameter of the propagule in question. Numbers of germinated and non-germinated conidia in arbitrarily-selected fields of view or in parallel transects, defined with an ocular micrometer, were counted. A minimum of 300 conidia were counted to provide an accurate estimate. It is desirable to determine the viability of propagules on replicate cultures and at various positions on the same plate.

This allowed calibration of the seed-coating techniques to obtain similar levels of *Trichoderma* loadings on the seeds for each coating method.

1.3. Seed Germination. One batch (5 seeds) of seeds from each treatment was placed on seed test paper (Whatman 181) in a 9 cm Petri dish. Dishes were sealed with Parafilm and held at 20° C. for 7-10 days and germination rate determined. This was repeated with untreated seed.

*Trichoderma* Selective Media (adapted from Williams, Clarkson et al 2003) was prepared as follows:

For 1000 ml
Basal Medium Ingredients:
0.2 g $MgSO_4$
0.9 g $K_2HPO_4$
0.15 g KCl
1.0 g $NH_4NO_3$
3.0 g glucose
0.15 g rose bengal
20 g agar
950 ml distilled water Basal Medium Process Mix liquid ingredients with all solid ingredients, except the agar in a 1 L Erlenmeyer flask. Add the 20 g agar and stir or shake. Plug with cotton wool and cover with foil. Autoclave.

Biocidal Medium (Per Litre)
0.25 g crystallized chloramphenicol
0.2 g quintozene
0.2 g captan
1.2 ml propamocarb (Previcur)
50 ml sterile distilled water Seed Weight Used as a measure of the homogeneity of the seed batch. Eight replicates of 25 seeds are weighed and the coefficient of variation (Cv) recorded. This coefficient should not exceed a value of 5. If it does then the procedure is repeated and the mean of all 16 samples used to calculate the number of seeds per gram.

| Crop | Mean Weight (g) | SD | Cv | TGW (g) |
|---|---|---|---|---|
| Radish | 0.223 | 0.009 | 4.216 | 8.9215 |

Results

Direct Enumeration Counts Using Haemocytometer

Initial Spore Density of *Trichoderma harzianum* dry spore preparation (at 5% moisture content), determined using haemocytometer, was $7.75 \times 10^9$ spores $g^{-1}$ (n=4,±2.6× $10^7$ 95% CL).

Spore Counting of Seed Wash

| Variable | Spore % | N | Mean | SE Mean |
|---|---|---|---|---|
| SporeCount | 9 | 4 | 327500 | 38379 |
| | 25 | 4 | 452750 | 37983 |
| | 50 | 4 | 844000 | 44678 |
| | 100 | 4 | 912250 | 16963 |

See FIG. 1.

There was a clear and statistically significant difference between the mean spore counts per seed achieved by the different treatments as determined by one-way ANOVA ($F(3,12)=63.68$ p=<0.001), although no significant difference was observed between the 100% spore and 50% spore treatments, or between the 25% spore and 9% spore treatments. All treatments exceeded the target of $10^5$ spores $seed^{-1}$.

| % Spores | Mean Spore Count $Seed^{-1}$ | *Expected Spore Count | As a % of 100% Treatment | **As a % of Expected | t value | p value |
|---|---|---|---|---|---|---|
| 100%* | 912250 | n/a | n/a | n/a | n/a | n/a |
| 50% | 844000 | 456125 | 93% | 185% | 10.21 | 0.002 |
| 25% | 452750 | 228063 | 50% | 199% | 5.03 | 0.015 |
| 9% | 327500 | 82103 | 36% | 399% | 14.47 | 0.001 |

*Expected Spore Count is calculated from the mean spore count achieved by the 100% Treatment, assuming a perfect distribution. Therefore the 50% Treatment would be expected to result in half the spores of the 100% Treatment, and so on.
**Essentially a measure of improvement in spore adhesion efficiency.

The addition of Entostat appears to improve the efficiency of spore adhesion to seed as the actual mean counts significantly exceed the expected results based on the 100% spore treatment (t-test).

Germination Determination

Mean Conidia Germination (from a Sample of 300)
Fresh conidia—275.75±5.56, n=4
Seed wash conidia—274.50±12.61, n=4

There was no statistically significant difference between the viability of fresh conidia and those washed from seeds as determined by one-way ANOVA ($F(1,6)=0.03$, p=0.862).

Enumeration Estimate from CFU Counts
Comparison of Haemocytometer and CFU (Corrected for Dilution) Counts

| Treatment | N | Mean | SE Mean | Grouping (using Tukey method) |
|---|---|---|---|---|
| 100 CFU | 4 | 894010 | 20287 | A |
| 100 Haemo | 4 | 912250 | 16963 | A |
| 50 CFU | 4 | 850557 | 24461 | A |
| 50 Haemo | 4 | 844000 | 44678 | A |
| 25 CFU | 4 | 443791 | 33682 | B |
| 25 Haemo | 4 | 452750 | 37983 | B |
| 9 CFU | 4 | 326345 | 33007 | B |
| 9 Haemo | 4 | 327500 | 38379 | B |

Means that do not share a letter are significantly different.

There was a statistically significant difference between groups as determined by one-way ANOVA ($F(7,24)=66.89$, p=<0.001). A Tukey post-hoc test revealed that no significance differences existed between the 100% and 50% groups, or between the 25% and 9% groups. The former may be explained by the loss of spores from the seed compared to the improved delivery when using Entostat.

Summary

Radish seed can be coated with *Trichoderma* spores in excess the target $10^5$ spores $seed^{-1}$ for all treatments.

Use of Entostat increases the efficiency of spore delivery as a result of a reduction in wasted or lost spores.

The germination viability of the spores was unaffected by their use as a seed coating.

Enumeration through direct counting of spores using a haemocytometer or through the use of CFU counting gives statistically similar results and therefore either method may be used once germination viability has been proved unaffected by the treatment.

The described method for radish as provided above is used to assess the delivery efficiency of spores by Entostat to seeds of green cabbage, broccoli, carrot and cauliflower. Similar results are obtained.

Effects of Seed Coating on Disease Suppression

Seeds are coated with *Trichoderma* using water or Entostat to achieve loadings of ca. $10^4$ and $10^5$ CFUs seed$^{-1}$. Water treatments are suspensions of spores in sterile water in which the seed samples are soaked for one hour. Seeds are then dried back, a likely commercial scenario, or sown wet coated. Entostat is applied at ratios of 3:1, and 9:1, Entostat to spores respectively. Seed treatment methods are then compared for their ability to protect germinating radish seedlings from *Pythium* spp., the causal agent of damping off disease in radish.

Inoculation of seeds with *Trichoderma*. Radish cv. Cherry Belle is inoculated as follows (target concentration per seed):

1) *Trichoderma* at $10^4$/seed using a water suspension (wet coating)
2) *Trichoderma* at $10^5$/seed using a water suspension (wet coating)
3) *Trichoderma* at $10^4$/seed using a water suspension (dry coating)
4) *Trichoderma* at $10^5$/seed using a water suspension (dry coating)
5) *Trichoderma* at $10^4$/seed using Entostat at 3:1
6) *Trichoderma* at $10^5$/seed using Entostat at 3:1
7) *Trichoderma* at $10^4$/seed using Entostat at 9:1
8) *Trichoderma* at $10^5$/seed using Entostat at 9:1
9) No *Trichoderma*, water only
10) No *Trichoderma*, Entostat only
11) Seed only Enumeration. *Trichoderma* is quantified using standard dilution plating methods on *Trichoderma* specific media. This confirms CFU loadings per seed for treatments 1-8. Dilution platings are carried out in duplicate.

*Pythium* Bioassay

Inoculum Preparation—*Pythium* sp., known to be pathogenic to radish, carrot, and cruciferous vegetables, is grown on PDA plates from stock cultures, and incubated at 20° C. to produce actively growing colonies. Agar plugs are removed from the plates and used to inoculate sterilised (autoclaved at 121° C. for 20 mins) John Innes No. 2 potting mix (80% moisture content; 60 g) mixed with potato cubes (2 mm$^2$, 25 g) in 500 ml Erlenmeyer flasks. Flasks are incubated at 20° C. for 14 days. Inoculum levels in the medium are quantified using a dilution plating method.

Effectiveness of Seed Treatment on *Pythium*.

Seeds are sown into individual cells of seed trays containing *Pythium*-inoculated medium (approx. 15 ml/cell). Four replicate batches of ten seeds per treatment are planted into the cells. Once sown, the trays are placed in a plant growth chamber (Weiss Gallenkamp Fitotron SG120) at 20° C. with ca. 16 h lighting. Cells are bottom watered. The number of seedlings surviving is recorded every 3 days for 21 days.

Time to emergence, percentage successful emergence and percentage plants expressing symptoms (including lesions and cankers) are recorded and the results analysed. Differences in Entostat treated seed and untreated seed are observed.

The described method for radish as provided above is used to assess time to emergence, percentage successful emergence and percentage plants expressing symptoms are recorded for seeds of green cabbage, broccoli, carrot and cauliflower. Similar results as obtained for Entostat treated and untreated radish seed are obtained. Differences in Entostat treated seed and untreated seed are observed.

The invention claimed is:

1. A vegetable plant structure product form comprising:
    i) a coating composition in powder form, the coating composition consisting of:
        (1) solid particles made throughout of at least one organic carrier material and having a volume mean diameter of ≥5 µm, wherein the carrier material is selected from waxes having a melting point of ≥50° Centigrade, and
        (2) one or more biological agents that possess an activity against at least one or more pathogens of a vegetable plant; and
    ii) a vegetable plant structure,
    wherein said vegetable plant structure is coated with the coating composition of i).

2. The vegetable plant structure product form according to claim 1, wherein the plant structure is that of a seed of a vegetable plant.

3. The vegetable plant structure product form according to claim 1, wherein the particles have a volume mean diameter in the range of 8 to 200 µm.

4. The vegetable plant structure product form according to claim 1, wherein the biological agent is selected from a chemical agent and a live biological agent or is a mixture thereof.

5. The vegetable plant structure product form according claim 1, wherein the organic carrier material is selected from carnauba wax, beeswax, montan wax, Chinese wax, shellac wax, spermaceti wax, candelilla wax, castor wax, ouricury wax and rice bran wax or is a mixture of two or more thereof.

6. The vegetable plant structure product form according to claim 1, wherein the biological agent is at least one biological antagonist present in the form of bacterial spores and/or fungal spores located on the surface of the said particles.

7. A method of coating a vegetable plant structure with a coating composition that consists of an organic carrier material comprising an organic wax in particulate form selected from waxes having a melting point of ≥50° Centigrade, wherein the particles of wax have a volume mean diameter of ≥5 µm, and a biological agent having an activity against one or more of fungal pathogens, bacterial pathogens and arthropod pathogens, the method comprising adding the biological agent to the organic carrier material, mixing the two together and applying the resulting composition to the vegetable plant structure.

8. The method according to claim 7, wherein the coating composition is applied in dry particulate form to vegetable plant structures that are vegetable seeds in dry particulate form.

9. The method according to claim 7, wherein the organic carrier material is selected from carnauba wax, beeswax, montan wax, Chinese wax, shellac wax, spermaceti wax, myricyl palmitate, cetyl palmitate, candelilla wax, castor wax, ouricury wax, wool wax, sugar cane wax, retamo wax and rice bran wax or is a mixture of two or more thereof.

10. The method according to claim 7, wherein the biological agent is selected from chemical insecticides and acaricides, fungicides, bactericides and live biological agents.

11. The method according to claim 7, wherein the biological agent is a live biological agent selected from *Pseudomonas* spp.,*Trichoderma* spp., Streptomyces spp., *Bacillus* spp., *Burkholderia* spp. and *Gliocladium* spp.

12. The method according to claim 7, wherein the biological agent is a live biological agent selected from P. syringe, P. fluorescens A506, T. viride, *Streptomyces lydicus, Ampelomyces quisqualis* isolate M-10, *Bacillus subtilis* GB03, *Bacillus pumilus* GB34, *B. Lichenformis*, and *B. megaterium, B. cepaciatype* Wisconsin, *Coniothyrium minitans, Agrobacterium radiobacter* Strain 84, *Streptomyces griseoviridis* strain K61, *Agrobacterium radiobacter* K1026, *G. catenulatum, Trichoderma harzianium* Rifai strain KRL-AG2 (T-22), *Bacillus subtilis* GB03 or *Bacillus pumilus* GB34, and *Gliocladium virens* (a.k.a. *Trichoderma virens*) GL-21.

13. The vegetable plant structure product form according to claim 1, wherein the particles are applied directly to the vegetable plant structure product form.

14. A vegetable plant structure product form comprising:

i) a coating composition in powder form, the coating composition consisting of:

(1) particles consisting of at least one organic carrier material and having a volume mean diameter of ≥5 μm, wherein the carrier material is selected from waxes having a melting point of ≥50° Centigrade, and (2) one or more biological agents that possess an activity against at least one or more pathogens of a vegetable plant; and ii) a vegetable plant structure, wherein said vegetable plant structure is coated with the coating composition of i).

* * * * *